United States Patent [19]

Chopin et al.

[11] Patent Number: 5,129,390
[45] Date of Patent: Jul. 14, 1992

[54] PROCESS FOR REGULATING AN ARTIFICIAL VENTILATION DEVICE AND SUCH DEVICE

[75] Inventors: Claude Chopin, Attiches; Marie-Christine Chambrin, Wattignies; Hervé Barancourt; Nicolas Floquet, both of Villeneuve d'Ascq, all of France

[73] Assignee: Institut Nationale de la Sante et de la Recherche Medicale, Paris, France

[21] Appl. No.: 397,479

[22] PCT Filed: Dec. 13, 1988

[86] PCT No.: PCT/FR88/00605
§ 371 Date: Aug. 16, 1989
§ 102(e) Date: Aug. 16, 1989

[87] PCT Pub. No.: WO89/05669
PCT Pub. Date: Jun. 29, 1989

[30] Foreign Application Priority Data

Dec. 18, 1987 [FR] France .................. 87 18327

[51] Int. Cl.$^5$ .............. A61M 16/00; A62B 7/04; F16K 31/26; F16K 31/02
[52] U.S. Cl. .................. 128/204.21; 128/204.23; 128/204.26
[58] Field of Search ............. 128/204.21, 204.23, 128/204.18, 204.26

[56] References Cited

U.S. PATENT DOCUMENTS

| 3,794,026 | 2/1974 | Jacobs | 128/204.26 |
|---|---|---|---|
| 3,961,627 | 6/1976 | Ernst et al. | 128/145.8 |
| 4,036,221 | 7/1977 | Hillsman et al. | 128/204.23 |
| 4,141,356 | 2/1979 | Smargiassi | 128/204.23 |
| 4,206,754 | 6/1980 | Cox et al. | 128/204.23 |
| 4,340,044 | 7/1982 | Levy et al. | 128/204.21 |
| 4,340,045 | 7/1982 | Manley | 128/204.26 |
| 4,444,201 | 4/1984 | Itoh | 128/204.23 |
| 4,481,944 | 11/1984 | Bunnell | 128/204.18 |
| 4,539,984 | 9/1985 | Kiszel et al. | 128/204.23 |
| 4,570,631 | 2/1986 | Durkan | 128/204.23 |
| 4,648,395 | 3/1987 | Sato et al. | 128/204.23 |

(List continued on next page.)

FOREIGN PATENT DOCUMENTS

| 0046570 | 3/1982 | European Pat. Off. |
| 0080155 | 6/1983 | European Pat. Off. |
| 8702566 | 5/1987 | PCT Int'l Appl. |
| 2079984 | 1/1982 | United Kingdom |

OTHER PUBLICATIONS

Puritan Bennett 7200, "Series Microprocessor Ventilator", Form AA-214 (Aug. 1987), Printed in U.S.A., 21488.

(List continued on next page.)

Primary Examiner—Edgar S. Burr
Assistant Examiner—Kimberly L. Asher
Attorney, Agent, or Firm—Sandler, Greenblum, & Bernstein

[57] ABSTRACT

The invention concerns a process for regulating a respiratory apparatus and the respiratory apparatus itself. The apparatus permits a succession of respiratory cycles depending on patient requirements, such as frequency FR (or respiratory rate RR). The succession of respiratory cycles consists of an inspiration phase, during which the patient is supplied with a current tidal volume (VT) of respirable gaseous fluid, and an expiration phase. The patient has his/her own natural spontaneous respiration, and the pressure in the patient's respiratory passages is defined as Paw. According to the the process, a theoretical respiration volume per minute value, called Vmn optical, is established as a function of the patient's condition and natural spontaneous respiration. Other values are also set or calculated. A minimum current tidal volume (VTmin) and a maximum allowable airway passage pressure, Paw max, are established. The total current tidal volume VT supplied to the patient during each respiratory cycle is monitored, and the artificial respiration is controlled to be within the set values VTmin and Paw max, and to satisfy the relation $Vmn\ optimal = FR \times VT$ in order to vary automatically the artificial respiration from spontaneous breathing to controlled breathing, or vice versa, as a function of the patient's natural spontaneous respiration.

16 Claims, 5 Drawing Sheets

U.S. PATENT DOCUMENTS

| | | | |
|---|---|---|---|
| 4,671,297 | 6/1987 | Schulze, Jr. | 128/716 |
| 4,686,974 | 8/1987 | Sato et al. | 128/204.23 |
| 4,686,975 | 8/1987 | Naimon et al. | 128/204.23 |
| 4,705,034 | 11/1987 | Perkins | 128/204.26 |
| 4,823,788 | 4/1989 | Smith et al. | 128/205.24 |
| 4,873,971 | 10/1989 | Perkins | 128/204.23 |
| 4,883,050 | 11/1989 | Urman et al. | 128/204.23 |
| 4,905,688 | 3/1990 | Vicenzi et al. | 128/204.25 |
| 4,932,402 | 6/1990 | Snook et al. | 128/204.23 |
| 4,938,212 | 7/1990 | Snook et al. | 128/205.24 |

OTHER PUBLICATIONS

Puritan Bennett 7200a, "Option #20 DCI", Form AA-991, (Dec. 1987), Printed in U.S.A., 99187.
Puritan Bennett 7202, "Display Accessory", Form AA-1143, (Dec. 1987), Printed in U.S.A., 114387.
Puritan Bennett "7200 Series", Form A-DAA498-02, (Jul. 1988), Printed in U.S.A., 48888.
Puritan Bennett, 7200 Series, "Option 10. Pressure Support", Form AA-763, (Mar. 1989), Printed in U.S.A., 76389.
Puritan Bennett, 7200 Series, "Pulse Oximetry", Form AA-1308, Printed in U.S.A., 130888.
Puritan Bennett, 7200a, "Option #30/40 Respiratory Mechanics", Form AA-985, (Jan. 1987), Printed in U.S.A., 98587.
Puritan Bennett, 7200a, "Option #50 Flow-By", Form AA-1144, (Jan. 1987), Printed in U.S.A., 114487.
Copy of International Search Report for PCT Application No. PCT/FR88/00605 with Annex.
Puritan Bennett, "Enter the Expanding World of the 7200a", Form AA-992, (Sep. 1988), Printed in U.S.A., 99288.
Puritan Bennett, "Effects on the Work of Breathing..", Form AA-1495, (Nov. 1989), Printed in U.S.A., 149589.
*Ventilators Theory and Clinical Application*, Yvon G. Dupuis, C. V. Mosby Co., 1986, Ch. 19-"The Puritan-Bennett 7200 microprocessor Ventilator", pp. 291-311, 19.
Puritan Bennett, "Pedestal Storage Compartment", Form AA-934, (Mar. 1984), Printed in U.S.A., 93484.
Puritan Bennett, "Wall Air Water Trap", Form AA-639, (Jun. 1987), Printed in U.S.A., 63987.
Puritan Bennett, "Single-Patient Use Exhalation Bacteria Filter", Form AA-1236, (Oct. 1987), Printed in U.S.A., 119487.
Puritan Bennett, "Support Program", Form AA-910, (Jun. 1988), Printed in U.S.A. 91088.

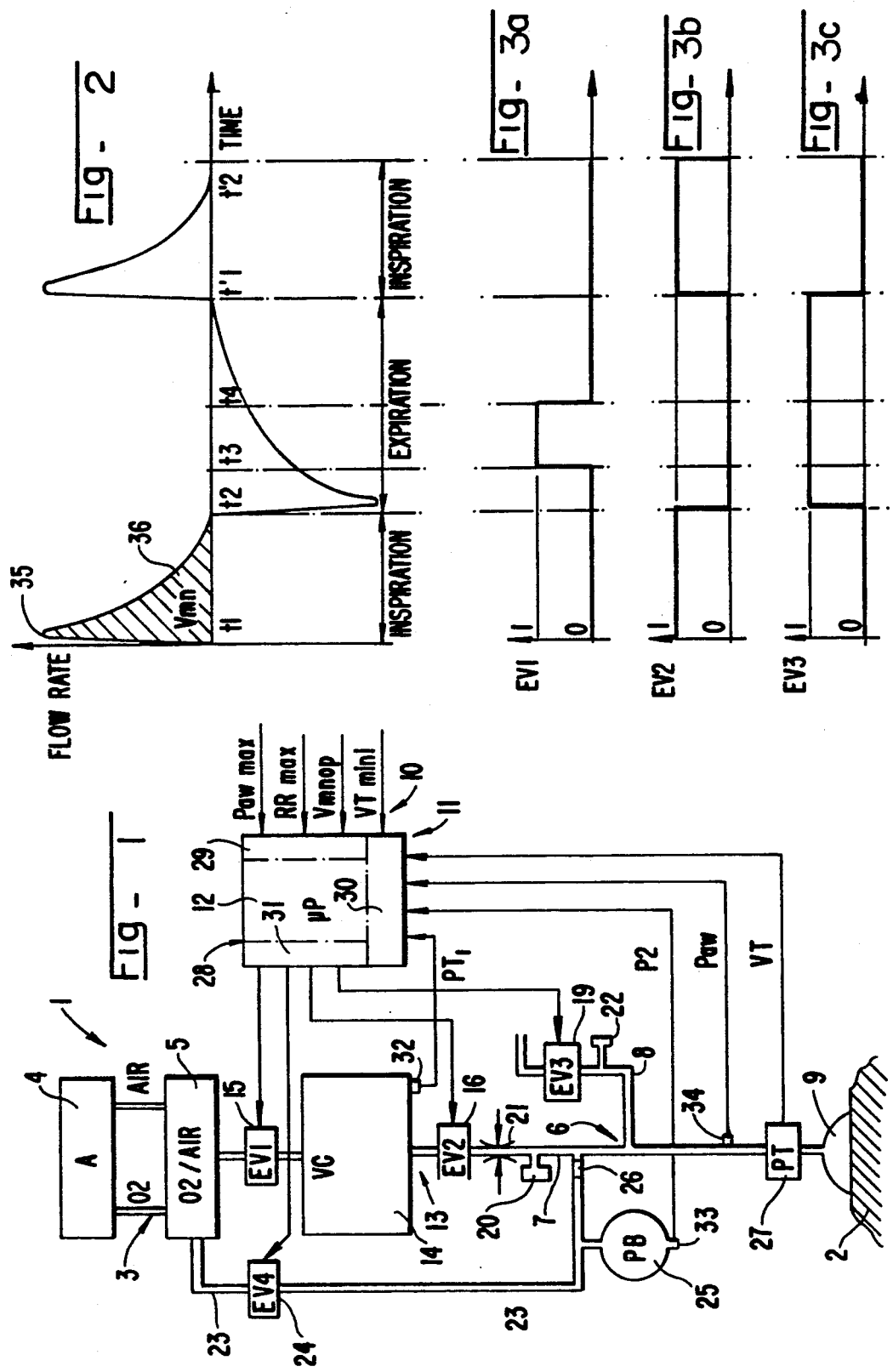

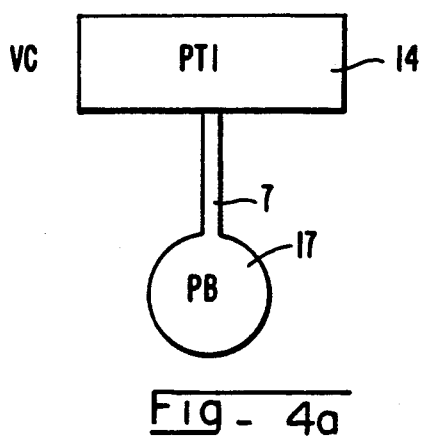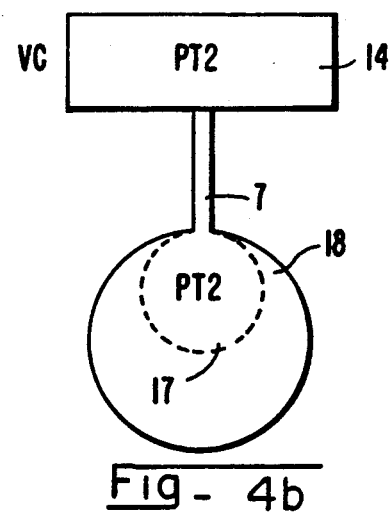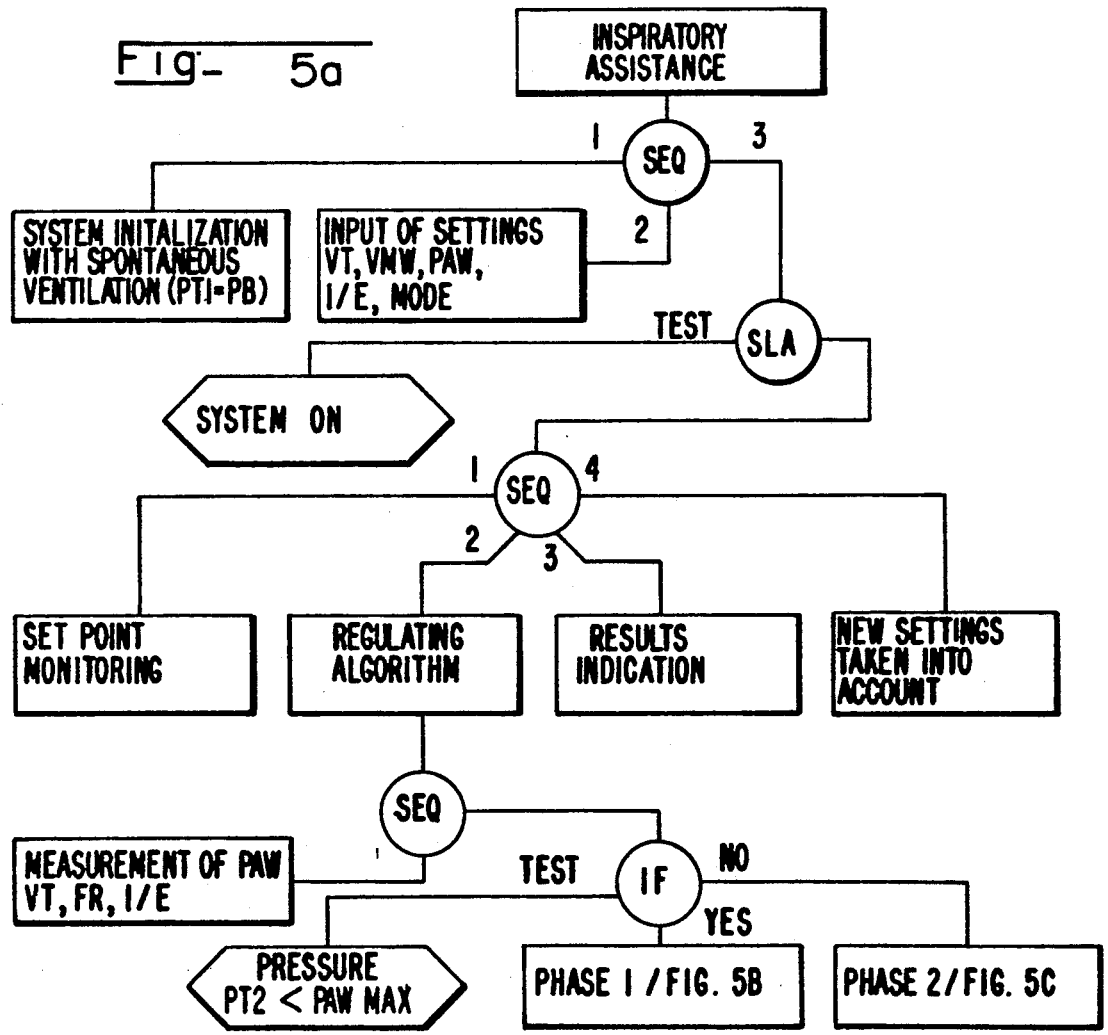

PROCESS FOR REGULATING AN ARTIFICIAL VENTILATION DEVICE AND SUCH DEVICE

BACKGROUND OF THE INVENTION

1. Field of the Invention

The invention relates to a process for regulating an artificial ventilating device and such device. The invention will be used in particular in the field of construction of medical equipment and in particular equipment to assist patients' inspiration.

2. Discussion of the Background and Pertinent Information

It is customary in the medical field to use a technique known as "Inspiration Assistance" or "Artificial Ventilation" in various cases, in particular when faced with neurological problems, respiratory failure and even during surgical operations and in post-operative phases. These techniques have been known for some considerable time, and endeavors are increasingly being made to reduce the barometric aggression for the patient when inspiration assistance is provided. Indeed, it should be noted that when a healthy individual has spontaneous natural ventilation, the individual causes inspiration by an internal negative pressure and expiration by compression of the volume of air in his or her airways or respiratory passages.

On the other hand, when under artificial ventilation, during the inspiration phase, a respirable gaseous fluid mixture is insufflated to the patient; the individual's airways are accordingly under positive pressure during the inspiration phase, and not under negative pressure as occurs naturally during spontaneous ventilation.

There is a known respiratory assistance device in which the artificial ventilation is controlled. In such device, the controlled ventilation acts as a prosthesis taking over the whole of the patient's ventilatory work. This is called total controlled ventilation.

Other ventilation techniques have been introduced which enable the patient to progressively take part in performing their respiratory function. One known assisted ventilation method utilizes auto-triggered ventilation and inspiration assistance. In this method, the negative pressure caused by this patient's inspiration triggers an inspiration phase either with a volume and duration fixed by the machine, or with the necessary gas flow rate to maintain a desired positive pressure which may be set by an operator.

Such known types of assisted ventilation have numerous disadvantages based primarily on the fact that the patient has to provide substantial inspiratory work, depending on the machine. Further, risks may be caused by such ventilation, such as risks of tachypnea, respiratory alkalosis, or hyperinsufflation.

More recently, other types of artificial ventilation such as closed loop type have been developed with the aim of avoiding an excessively abrupt change from totally controlled ventilation to exclusively natural spontaneous ventilation, to enable the patients to adapt gradually and increase his or her security. Among these are intermittent controlled ventilation, variable imposed ventilation, or the method of $CO_2$ closed loop ventilation.

In an intermittent controlled ventilation device, there is imposed on the patient, for example, n control cycles to x spontaneous cycles. This type of ventilation has disadvantages residing in the difficulty of setting adjustment and the need for manual intervention to adjust the device as a function of the way in which resuscitation develops.

In a variable imposed ventilation method, the ventilation is controlled by a minimum ventilation per minute setting. In this device, a threshold number of liters of gaseous mixture insufflated per minute is set, and whenever the patient's ventilation falls below this threshold, the ventilator delivers the necessary number of controlled cycles to achieve this threshold. The main inconvenience or disadvantage of this type of imposed ventilation is reflected by the adverse risks that could be produced, such as tachypnea and/or hypercapnia due to a possible increase of $CO_2$ level in arterial blood.

Analysis of the problems posed by inspiratory assistance for patients reveals the usefulness of limiting the aggressiveness of ventilation, and in an addition permanently directing artificial ventilation to take maximum account of the patient's spontaneous natural ventilation. This allows the patient to take over part of his or her respiratory work and thereby assist in rehabilitation and/or allows weaning or severance from the ventilatory assistance.

Known inspiratory assistance devices are disadvantageous in that manual intervention is frequently required by medical personnel as the devices are not regulated correctly to enable the inspiratory assistance to be adjusted in accordance with the efforts being made by the patient. Further, these types of devices are not without risk of hypo-ventilation or hyperventilation, as volume delivered during the insufflation phase is not entirely controlled.

An object of this invention is to provide an artificial ventilation device and a process for regulating an artificial ventilation device for patient inspiratory assistance which enable the various above-mentioned disadvantages of the known devices to be overcome.

One of the objects of this invention is to provide a process for regulating an artificial ventilation device which carriers out an intermediate mode of artificial ventilation between a current controlled ventilation mode and a natural spontaneous ventilation mode. This intermediate mode is carried out as a function of the patient's performance, and to takes into account the patient's own spontaneous ventilation.

This additional intermediate mode therefore makes it possible to conceive of a workable system capable of changing automatically between the two extreme modes of ventilation, i.e., from spontaneous ventilation to controlled ventilation, or vice-versa.

Another object of this invention is to provide a process for regulating an artificial ventilation device and a device for aiding the patient's inspiration in which the total tidal volume of respirable gaseous insufflated into the patient in each cycle is controlled.

Another object of this invention is to propose an artificial ventilation device for assisting the inspiration of a patient which, in particular, thanks to its regulating process, enables the insufflation characteristics to be improved by providing the patient with maximum inspiratory assistance when the effort required is maximum, i.e., at the start of inspiration.

Another object of this invention is to provide a regulating process for an artificial ventilation device and a device using it enabling the manual intervention on the part of the intensivist (i.e., the person attending and monitoring the artificial ventilation device and patient) to be minimized, relieving him or her of any requirements of readjustment in accordance with developments of resuscitation.

Other objects and advantages of the this invention will become evident during the course of the description that follows, which is given as a guideline only and which is not intended to limit the invention.

According to the invention, a regulating process is provided to regulate an artificial ventilation device to assist the volumetric inspiration of a patient. The artificial ventilation device allows a sequence of respiratory cycles as a function of the patient's requirements, such as frequency of respiration FR or respiratory rate RR. Each cycle can consist of an inspiration phase, during which the patient is administered a volume of respirable gaseous fluids referred to as the tidal volume VT, and an expiration phase. The patient exhibits his or her own natural spontaneous ventilation and an airway pressure PAW.

A theoretical satisfactory (i.e., optimum) value is set for the patient as a function of his or her condition and natural spontaneous ventilation. This theoretical satisfactory ventilation value is referred to as the optimum ventilation per minute Vmn. A minimum tidal volume value VT min to be inspired by the patient is also set. Further, the patient's maximum airway pressure PAWmax is set. The total tidal volume VT delivered to the patient in each respiratory cycle is controlled by the disclosed artificial ventilation device. The artificial ventilation is controlled as a function of the minute ventilation setting Vmn, the minimum tidal volume VT min, and the maximum airway pressure PAWmax to satisfy the equation $Vmn = RR \times VT$, so that the artificial ventilation changes automatically from a spontaneous ventilation mode to a controlled ventilation mode, or vice versa, as a function of the person's spontaneous natural ventilation.

The artificial ventilation device of the present invention comprises a supply source or supply means for supplying respirable gaseous fluid. This supply source provides at least a pressurized amount of fluid supply at the time of artificial ventilation. In addition, means for piping the gaseous fluid to the patient are provided. The piping means comprise entering means for entering reference settings suitable for fixing an optimum theoretical ventilation per minute Vmn value for the patient, a minimum tidal value VTmin, and a maximum airway pressure value Paw max. The piping means further comprises a control means for controlling the total tidal value VT delivered to the patient in each respiratory cycle and a closed loop control means for controlling, in close loop fashion, the artificial ventilation of the device by, in each cycle checking the relationship $Vmn = RR \times VT$, and acting on the artificial ventilation pressurized fluid supply in accordance with the patient's spontaneous natural inspiration, in order to cause the artificial ventilation to change automatically between spontaneous ventilation and controlled ventilation.

The present invention will be easier to understand upon reading of the following description accompanied by the appended drawings which form an integral part hereof.

BRIEF DESCRIPTION OF THE DRAWINGS

FIG. 1 provides a schematic illustration of the artificial ventilation device for a patient's volumetric inspiratory assistance in accordance with this invention;

FIG. 2 shows a graph of the respirable gaseous fluid delivered to the patient by the artificial ventilation device in this invention as a function of time;

FIGS. 3A-3C show a diagram of the phases of the various control signals of the artificial ventilation device used in obtaining the respirable gaseous flow as depicted in FIG. 2, the abscissae thereof corresponding in time to the graph represented in FIG. 2;

FIGS. 4A and 4B illustrate the physical principle of the inspiratory assistance delivered by the device of the present invention and supplying maximum assistance at the start of insufflation; and FIGS. 5A-5G schematically illustrate the operational organizational chart of an artificial ventilation device in accordance with this invention.

DETAILED DESCRIPTION OF THE PREFERRED EMBODIMENTS

Figure 5B:
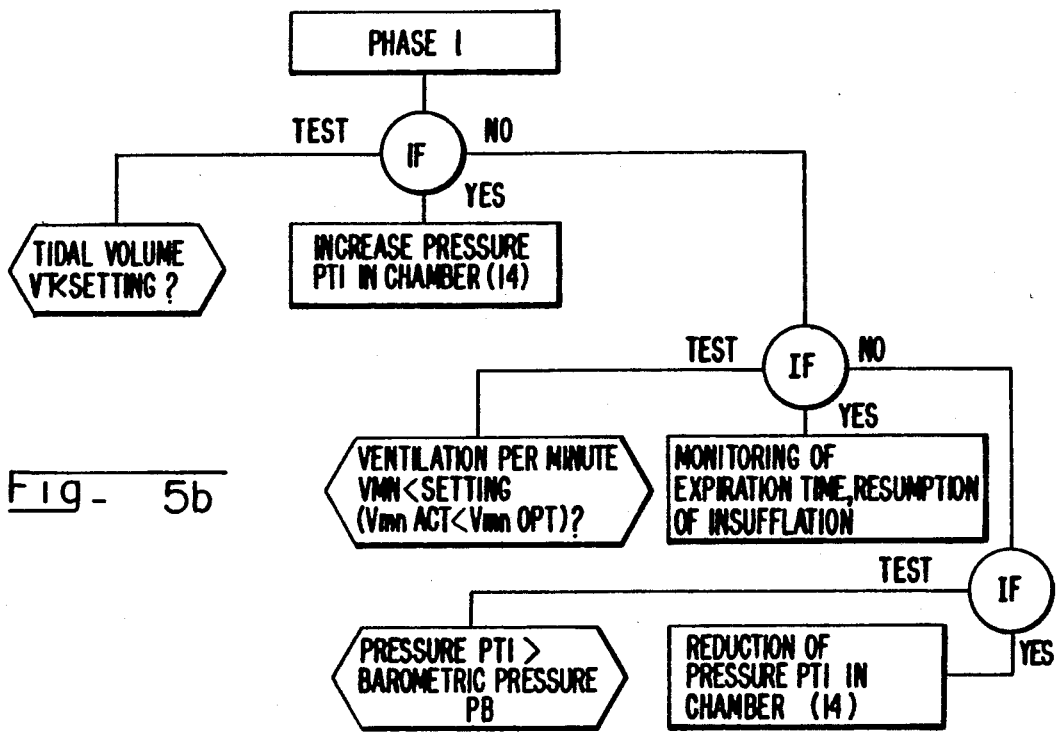

The invention relates to a process for regulating an artificial ventilation device and a ventilation device in particular using the same process, the process and device being applied in particular to provide volumetric inspiratory assistance for a patient.

In general, an artificial ventilation device allows a sequence or succession of respiratory cycles at a respiratory rate RR (or frequency FR), each cycle exhibiting an inspiration phase during which a volume of respirable gaseous fluid referred to as the total tidal volume VTtot is delivered to the patient for an insufflation time TI, and also exhibiting an expiration phase defined by an expiration time TE. The total tidal volume VT tot is the sum of the patient's spontaneous tidal volume VT pat and the tidal volume delivered by the artificial ventilation device VT mach.

During this inspiratory assistance, the patient exhibits his or her own natural spontaneous ventilation VT pat, and one of the objects of this invention is to allow operation of the artificial ventilation device as a function of the patient's requirements. For this purpose, in accordance with the artificial ventilation device and the process for regulating the device, the following steps are carried out.

First, a satisfactory or optimum theoretical ventilation value is set for the patient as a function of his or her condition and of his or her natural spontaneous ventilation. This satisfactory or optimum value is termed the optimum ventilation per minute VMN opt, and is determined by the intensivist or operator who sets this value as a function of the patient's requirements. Then, a minimum tidal volume VTmin to be inspired by the patient in each respiratory cycle is also set by the intensivist. This value is set in order to ensure satisfactory gaseous exchange during respiration.

The total tidal volume VTtot delivered to the patient in each respiratory cycle is monitored with the aid of any appropriate well-known means for detection, with the total tidal volume VTtot being greater than or equal to the minimum tidal volume VTmin.

For reasons of safety of the regulating process under the invention, a maximum airway pressure value Pawmax is set during the inspiration phase in order to limit the insufflation pressure to a maximum allowable for the patient.

Finally, artificial ventilation is controlled as a function of the optimum ventilation per minute VMNopt and the minimum tidal volume VTmin settings. The relationship $VMNopt = RR \times VTtot$ may be satisfied for various respiratory rates RR and values of VTtot as long as VTtot is greater than Vtmin, RR is greater than a minimum safety frequency, and the airway pressure is less than the maximum value PAWmax. The device of the invention passes automatically from spontaneous ventilation to controlled ventilation or vice-versa, as a function of the patient's natural and spontaneous ventilation.

In accordance with another aspect of the present invention, the artificial ventilation device is designed such that upon insufflation during the inspiration phase, it delivers maximum assistance at the start of inspiration by delivering a low pulmonary volume. It is noted that it is at the start of inspiration that the individual has to supply maximum effort to open the pulmonary alveoli. Thereafter, the effort needed to keep the pulmonary alveoli open is considerably less. The regulating process for the artificial ventilation device of the present invention will be described in greater detail, but to make it easier to understand, a method of producing an artificial device in accordance with the present invention will be described.

FIG. 1 shows a version of an artificial ventilation device 1 in accordance with the present invention which will be applied in particular for providing a patient 2 with volumetric inspiratory assistance. The device comprises at least means 3 for supplying respirable gaseous fluid by providing at least a supply of pressurized fluid during artificial ventilation. The means 3 of supplying act as a supply source and consist in particular of a supply 4 which can, for example, authorize pressure of up to approximately 3 bars. The supplying means 3 also comprise an oxygen-air mixer unit 5 which enables a respirable gaseous fluid to be produced of an adjustable concentration.

In addition, distribution means 6 are also provided for distributing the gaseous fluid to the patient. The distribution means comprises in particular an insufflation nozzle or part 7 and an expiration nozzle or part 8, which are both designed according to traditional techniques known in the trade. Distribution is made to the patient 2 at the patient's mouth via a T-tube 9 or any other suitable mask device.

According to another aspect of the present invention, the artificial ventilation device 1 comprises a number of elements in combination. Reference setting means 10 are provided for introducing reference settings, such as an optimum ventilation per minute value Vmn opt for the patient, a minimum tidal volume VT min and a maximum airway pressure value Paw max. Monitoring means 11 are also provided for monitoring the total tidal volume VT tot delivered to the patient in each respiratory cycle. Controlling means 12 controls the artificial ventilation, by in each cycle checking the equation Vmn opt = RR × VT tot and by affecting the pressurized fluid supply to the patient in accordance with the patient's spontaneous natural inspiration, to cause artificial ventilation to change automatically between a spontaneous ventilation and a controlled ventilation.

In addition, the artificial ventilation device 1 in accordance with another major aspect of the present invention, comprises delivering means 13 for delivering maximum assistance to the patient at the start of inspiration by, for example, delivering a low pulmonary volume during the inspiration phase upon insufflation with the device 1. More precisely, the delivery means 13 comprise a receiver chamber or tank 14 having a predetermined volume VC. The tank or chamber 14 is inserted at a point along the inspiration line 7 between the pressurized supply 3 and the patient 2 as shown in FIG. 1. In addition, the tank or chamber 14 is designed to withstand pressure so that, during operation of the device 1, the tank or chamber 14 may be filled with pressurized gaseous fluid during each respiratory cycle at a predetermined working pressure PT. Filling with pressurized gaseous fluid of the tank or chamber 14 is permitted by a solenoid value EV1 marked 15 which is inserted in series onto the tube or nozzle connecting the mixer 5 and the tank or chamber 14.

In addition, the delivery means 13 also comprises discharging means 16 for discharging the volume VC, which is provided at a pressure $PT_1$. The discharging means 16 is provided downstream of the tank or chamber 14 to allow it to empty quickly. The discharging means consist substantially of the solenoid valve EV2 marked 16 inserted in series with the inspiration line 7 which connects the patient's tube to the tank or chamber 14.

FIGS. 4A and 4B show the operating principle of the delivery means 13 which allow the provision of maximum inspiratory assistance at the start of insufflation by supplying a low pulmonary volume. In particular, FIG. 4A gives a schematic presentation of the tank or chamber 14, the pulmonary volume of the patient at the end of the expiration 17, and the insufflation line 7. At the end of expiration, it is assumed that the tank or receiver chamber 14, having a volume VC, is filled at a working pressure $PT_1$ as a function of the volume to be delivered to the patient.

While the solenoid valve EV2 is not open, the pressurized gaseous fluid in tank or chamber 14 is preserved at the pressure $PT_1$, given that it is not connected directly to the patient.

At the lungs, the barometric pressure PT 17 (FIG. 4A) is typically equal to the value of the patient's functional residual capacity FRC.

FIG. 4B shows the discharge phase of the pressurized gaseous fluid contained in the tank or chamber 14. At the start of insufflation, the solenoid valve EV2 which connects the tank or chamber 14 to the patient is open, so that the device delivers to the patient the tidal volume VT mach. At the insufflation, there is a resultant pressure $PT_2$ inside the tank or chamber 14. The pulmonary volume is equal to FRC+VT, and is shown schematically as 18 in FIG. 4B. VT represents the patient's insufflated tidal volume.

Accordingly, given the structure of the device as described, and as a result of the sudden discharge of the volume VT mach to the patient's lungs, there is a peak fluid flow at the start of insufflation as illustrated in FIG. 2. The flow insufflated to the patient by artificial ventilation as a function of time is shown in FIG. 2. The start of the inspiration phase, i.e., of insufflation, corresponds to time t1, and the end of the insufflation phase corresponds to time t2.

Given the physical law of discharge, a curve representing the flow rate is obtained having a peak 35 that is very close to the time t1 corresponding to the beginning of the discharge and then decays exponentially as indicated by the numeral 36 to establish an equilibrium state until the end of the inspiration time at t2.

The device of the present invention is also provided with a solenoid valve EV3 19, as shown in FIG. 1. The solenoid valve EV3 is provided on the expiration line 8 to enable the inspiration phase to work or function properly and also allow expiration.

FIGS. 3A to 3C show the respective states with respect to time of the three solenoid valves EV1 to EV3 during the successive phases of the inspiration and expiration. Inspiration takes place between the time reference at t1 and t2, and expiration takes place during the time between t2 and t'1. A value of 0 in any of the FIGS. 3A-3C represents that the solenoid valve is in its closed state, i.e., with the line blocked, and a value of 1 represents that the solenoid valve is in its open state to allow free communication between the elements of the device.

The operation of the device of the present invention is as follows. The solenoid valve EV1 is open during expiration solely for the time which it takes to fill the tank to the pressure PT1, i.e., between time t3 and t4. The solenoid valve EV2 is closed throughout expiration and open throughout insufflation. Solenoid valve EV3 on the other hand is closed throughout inspiration and open throughout expiration.

In accordance with a particular feature of the regulating process of the device of the present invention, a cycle cut-off or timing in the inspiratory phase and expiratory phase is controlled by detecting the instance or time of 0 (zero) flow at the end of inspiration and at the end of expiration by the patient. With regard to the operating sequence of the solenoid valves and of the discharge means for discharging the tidal volume VT mach, the open and closed signals which operate the solenoid valves EV2 and EV3 are given to correspond to the times at which there is no or 0 gaseous flow, that is, at time t1 and t2, t'1, etc.

The abscissa times indicated in FIGS. 2, and 3A-3C, are defined as follows: The duration t1-t2 is a function, as previously mentioned, of the times at which there is no gaseous flow. The duration t2-t3 is fixed as a constant. The duration t3-t4 is variable as a function of the working pressure PT which is to be achieved.

The inspiration line 7 is also provided with a pressure relief or over pressure valve 20 and a flow reducing means 21. The expiration line 8 also has an over pressure valve 22. In addition, the device is provided with a supply of respirable gaseous fluid at about barometric pressure level, suitable for supplying the patient for his or her spontaneous natural ventilation. This supply may be provided simply by venting the inspiration line 7 by means of an additional non-return air valve.

As shown in FIG. 1, a particular embodiment of the present invention provides a respirable gaseous fluid supply at about barometric pressure by using air mixed with oxygen. This respirable gaseous fluid is provided by mixer 5. The mixture of respirable gaseous fluids is supplied to the patient by means of line 23 which is provided with a solenoid valve EV4 24. The line 23, for example, supplies a flexible breathing bag 25 with the mixture at a pressure essentially close to barometric pressure. This bag 25 is then connected to the inspiration line 7 by a non-return valve 26, the technique and operation of which is known by those skilled in the art.

Thus, when solenoid valve EV4 is open, the flexible bag 25 will be filled at a pressure $P_z$ which is slightly higher than barometric pressure PB, with a flow of air enriched with oxygen, which is to be used in the phase of inspiration by spontaneous natural ventilation on the part of the patient. When artificial ventilation is in use, the non-return valve 26 will prevent the discharge of the tidal volume VT mach supplied from the tank or chamber 14 from being expelled through line 23. Thus, the entire quantity of the fluid discharged is directed toward the patient 2.

With this arrangement, when the patient's spontaneous natural ventilation is not sufficient, the device enables the patient to be supplemented by artificial ventilation during a mode referred to as an intermediate mode, the control of which is to be described below.

The ventilation device of the present invention is further provided with measuring facilities 27 are for measuring the flow of the fluid inspired and/or expired by the patient. The measuring means 27 located just upstream to the patient 2 and comprise a flow sensor of the pneumotachograph type. It is noted that the flow signal provided by the flow sensor can be integrated in order to ascertain the volume inspired or expired by the patient. In this respect, the device of the present invention further comprises processing means for processing the flow signal thus measured in order to, on the one hand, detect instants or times of 0 (zero) flow at the end of inspiration and/or expiration and, on the other hand, to determine the total tidal volume VT tot inspired by the patient as a function of the measured rate of flow.

In addition, pressures sensors 32-34 are provided and designed to measure in particular the working pressure of the tank or chamber 14, the pressure in the flexible bag 25, and the pressure of the airway Paw, respectively, as illustrated in FIG. 1.

In order to allow control of the regulating process according to the present invention, the artificial ventilation device comprises means for increasing and/or decreasing the artificial ventilation acting on the pressurized fluid supply 3, thereby enabling the condition of the equation Vmn opt=RR×VT tot to be met and maintained as a function of the patient's specific natural spontaneous supply of respirable gaseous fluid with respect to a reference setting. In this connection, calculation means 28 are provided which consist substantially of a microprocessor CPU, which enables various stages of the process of the present invention to be performed sequentially, input interface 29, 30, and output interface 31. Input interface 29, 30 gathers the reference values for the settings such as optimum ventilation per minute, minimum tidal value, maximum airway pressure, maximum respiratory pressure, and measured information such as the working pressure $PT_1$ in the tank 14, airway pressure Paw, inspiration and/or expiration rate, and possibly the working pressure in the flexible bag 25. Output interface 31 monitors the sequential control of solenoid valves 15, 16, 19, 24 to authorize or activate either spontaneous ventilation, total controlled ventilation, or intermediate artificial ventilation and/or the expiration phase.

Figure 5C:
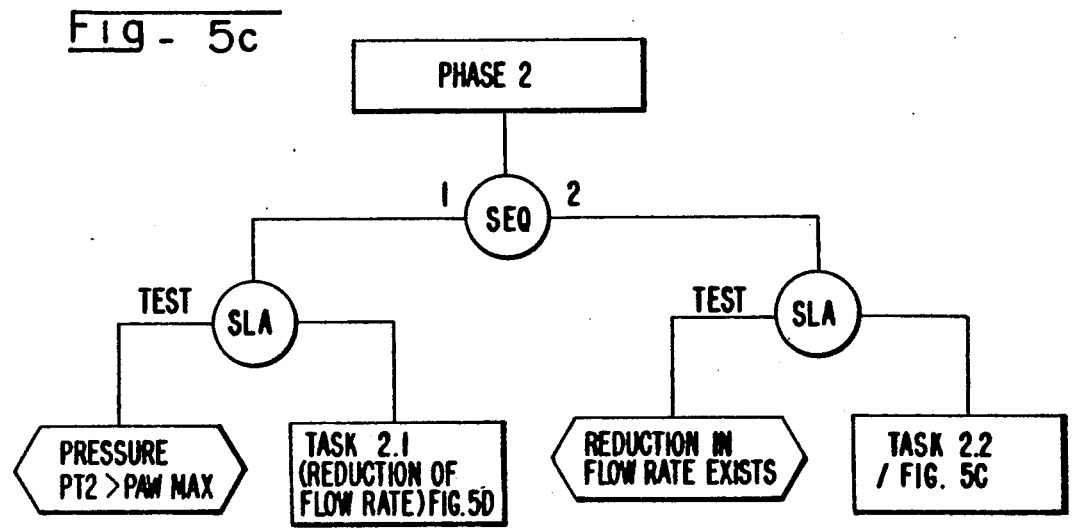
Figure 5D:
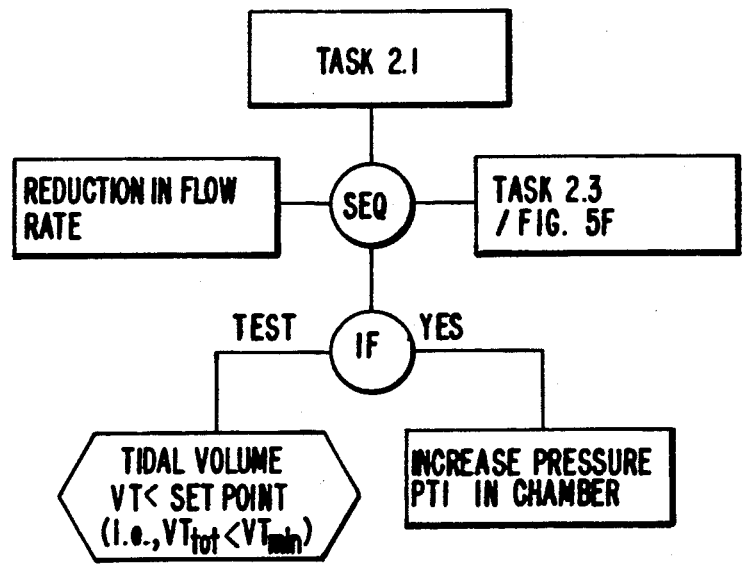
Figure 5E:
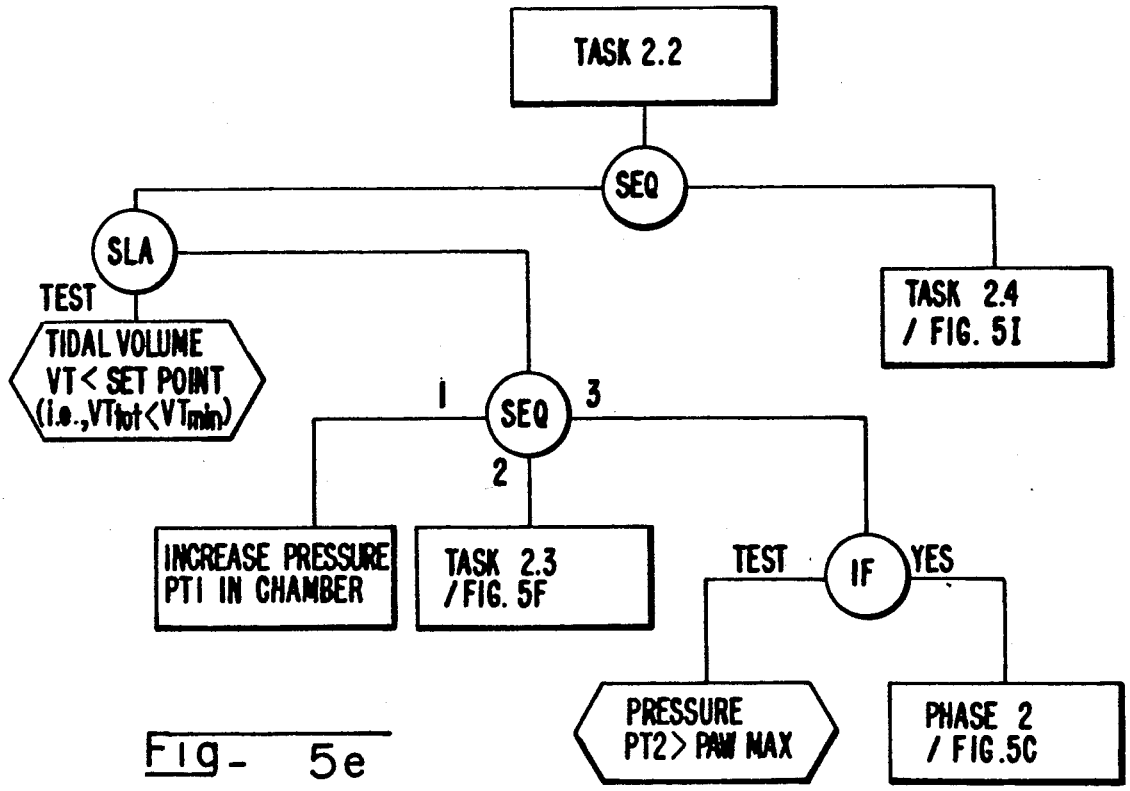
Figure 5F:
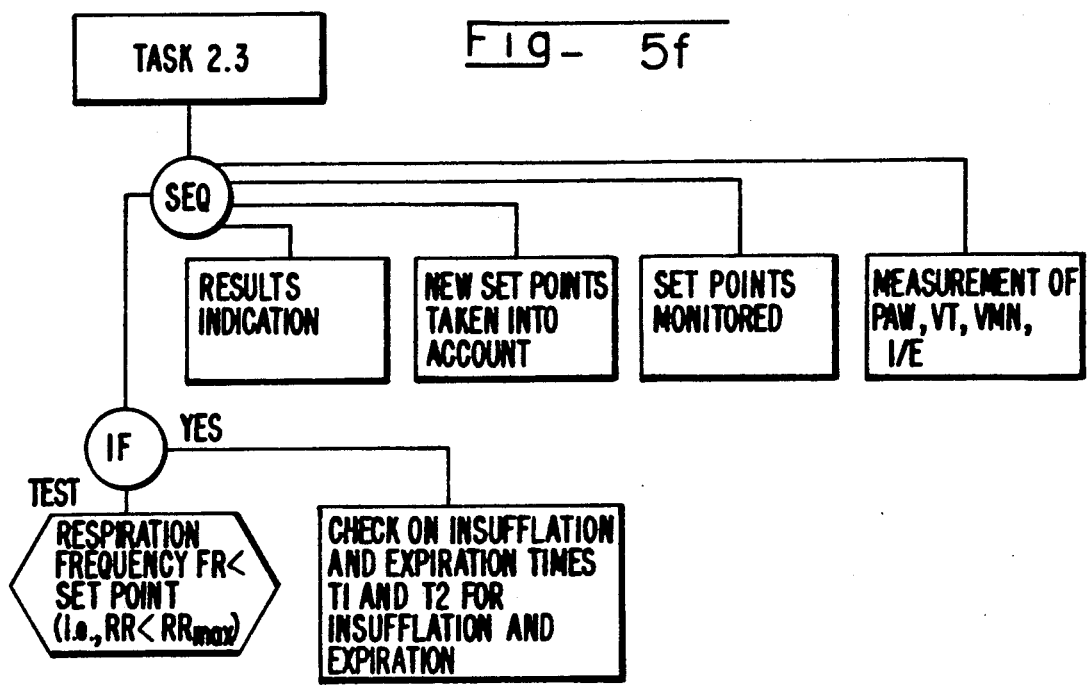
Figure 5G:
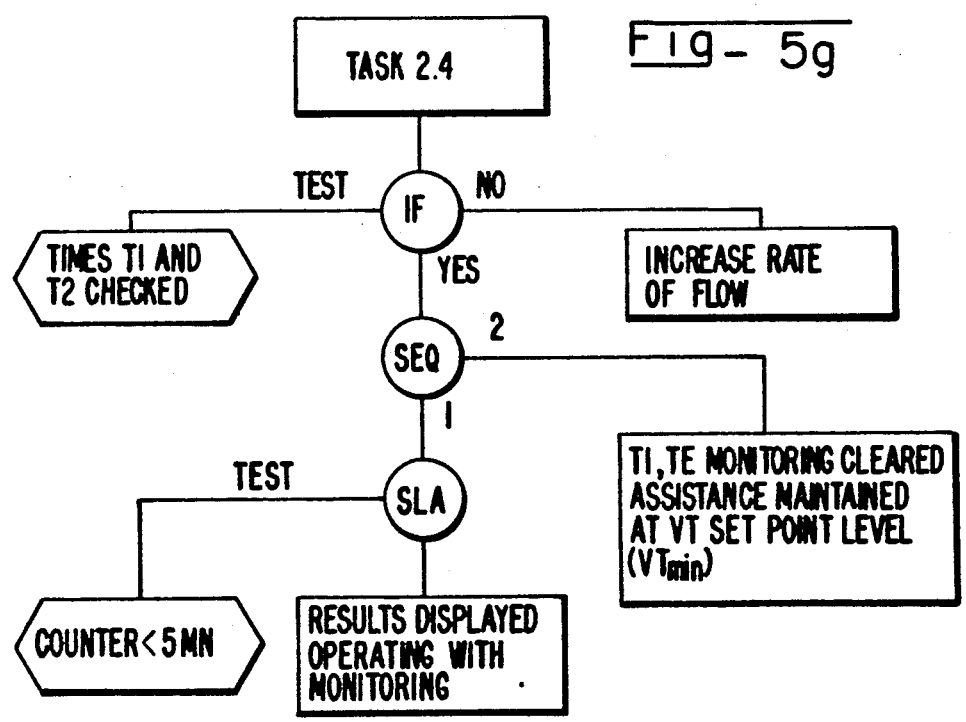

With regard to the regulating process for the device in accordance with the present invention, FIGS. 5A and 5G show flowcharts which schematically represent the sequence of controls of the inspiratory assistance device of the present invention. FIG. 5A shows the basic organization chart, and phases and 2 are illustrated in FIGS. 5B and 5C respectively. Similarly, with regard to FIG. 5C, tasks 2.1 and 2.2 are illustrated in FIGS. 5D and 5E respectively. FIGS. 5F and 5G show tasks or steps 2.3 and 2.4, respectively referred to in FIGS. 5D and 5E. The regulatory process or regulating process for the artificial ventilation device of the present invention will be described with reference to FIGS. 5A-5G.

In controlling the artificial ventilation device as shown in FIG. 1 of the present invention, the following steps are performed. First, the system is initialized while in spontaneous ventilation, and the pressure $PT_1$ in the tank or chamber 14 is set to be equal to PB. Then, a number of setting are inputted to the device including Vmn opt, VT min, Paw max, RR max, I/E, and MODE. Thereafter, so long as the system remains on, four additional sequential steps are performed. First, the set point is monitored. Thereafter, the regulating algorithm is performed. Third, the results are indicated. And fourth, new settings are taken into account.

In the step for regulating the algorithm, two other steps are then performed in sequence. First, Paw, VT, RR, and I/E are measured. Then, a test is performed to see whether the pressure PT2 is less than Paw max. If it is less than Paw max, phase 1 of the algorithm as shown in FIG. 5B will be performed. If it is not less than Paw max, phase 2 as shown in FIG. 5C will be performed.

In phase 1, as shown in FIG. 5B, it is determined whether the tidal volume VT is less than a set value. If it is less than the set value, the pressure PT1 in the chamber 14 is increased. If it is not, that is, if the tidal volume VT is not less than the set value, another test is performed.

In this other test, it is determined whether the ventilation per minute value vmn is less than a set value. If it is less than the set value, the amount of time for expiration is monitored, and the insufflation is resumed. If the ventilation per minute value is not less than the set value, another test is performed.

In this other test, it is determined whether the pressure PT1 is greater than the barometric pressure PB. If it is, the pressure PT1 in the chamber 14 is decreased.

Phase 2, as shown in FIG. 5C is performed as follows. First, as long as the pressure PT2 is greater than Paw max, task 2.1 as shown in FIG. 5D (reduction of flow rate) will be performed. Then, in phase 2, so long as there is a reduction in flow rate, task 2.2 as shown in FIG. 5C will be performed.

The task 2.1 of FIG. 5D first causes a reduction of flow rate. Then a test is performed, where it is determined whether the tidal volume VT is less than a set point. If it is less than a set point the pressure PT1 and the chamber 14 is increased. After performance of these steps, the program then proceeds to test 2.3 as shown in FIG. 5F.

Going back to task 2.2, as mentioned above with reference to FIG. 5C, this task is shown in FIG. 5E. First, a test is performed to see whether the tidal volume VT is less than a set point. So long as it remains less than the set point, a sequence of steps are performed. First, the pressure PT1 in the tank or chamber 14 is increased. Then, the task 2.3 depicted in FIG. 5F is performed. Finally, so long as the tidal volume VT remains less than the set point, a third step performing a test to see whether the pressure PT2 is greater than Paw mach is performed. If the pressure PT2 is greater than Paw mach, the algorithm or flowchart returns to phase 2 which was shown in FIG. 5C.

The second sequential main step of the task 2.2, which is performed so long as there is a reduction in flow rate, is the task 2.4 which is shown in FIG. 5I.

The task 2.3 is described as follows: First, a test is performed to determine whether the respiration frequency FR or the respiration rate RR is less than a set point. If it is less than the set point, the process will check on the insufflation and expiration times t1 and t2 for insufflation and expiration. Second, in task 2.3, the results are indicated. Third, new set points or set values are established. Fourth, the set values are monitored.

And finally, in performance of the test 2.3, the values Paw, VT, Vmn, and I/E are measured.

Test 2.4 which is the second main sequential step of the test 2.2, which was shown in FIG. 5E, is described as follows with reference to FIG. 5G.

First a test is performed to determine whether the times t1 and t2 have been checked. If they have, another test is performed to determine whether a counter indicates less than five minutes. As long as the counter indicates less than five minutes, the results are displayed and the system monitors. Then, if the times t1 and t2 have been checked, the values t1 and t2 are cleared, and the inspiration assistance is maintained at the VT set point level, i.e., VT min. If the times t1 and t2 are not checked or have not been checked, the rate of flow caused by the devices increase.

It is noted that the term seq is used to signify "performed sequentially", the term sla is used to signify "so long as", and the expression "if" signifies a condition.

The system is initialized during spontaneous ventilation, while the ventilation per minute VMN opt, minimum tidal value VT min and maximum airway pressure Paw max settings are fixed. Calculation of the tidal volume VT and the respiratory rate RR is carried out over 3 respiratory cycles. Testing is carried out in order to determine the certain settings in accordance with the following manner: During insufflation, the air pressure value Paw is constantly measured, since this is a safety setting. If the maximum value Paw mach is reached, the discharge solenoid valve EV2 is closed and the filling pressure of the tank or chamber 14 does not increase. It is to be noted, however, that a flow controlled procedure may be envisaged at this level, this procedure being included in the diagram shown in FIG. 5d.

If the patient him or herself stays within the settings to satisfy the equation $VMN\ opt = RR \times VT\ tot$, the artificial ventilation effect of the device is canceled. Otherwise, artificial ventilation is increased each cycle until such time as the patient meets the setting defined by the equation with inspiratory assistance.

Thus, the tidal volume VT tot insufflated by the patient is compared with a preset value. If this setting is not reached, the working pressure PT1 in chamber 14 is increased. This increase is carried out by a variable level of increments as a function of the difference between the measured value and the setting value to be achieved.

If the set tidal volume VT min is met, the ventilation per minute value vmn opt is tested. If this value is not proper, the patient's respiratory rate is too low, and the duration of expiration is thus monitored and inspiration is triggered in such a way as to comply with a minimum desired respiratory rate value RR min.

If on the other hand, the set tidal volume set VT min is exceeded and inspiratory assistance is being given, the inspiratory assistance is reduced.

In effect, when the set point VT min is reached with inspiratory assistance, artificial ventilation is progressively decreased, while still maintaining control, until such time as the patient regains his or her natural spontaneous ventilation mode. On the other hand, to provide maximum assistance at the start of inspiration, in each inspiration phase, and during an artificial ventilation mode, the discharge of a gaseous given volume VT mach of respirable fluid, previously brought to a preset working pressure PT1, is insufflated to the patient. As described earlier, the volume VT mach, is obtained from the tank or chamber 14 filled at a pressure $PT_:$, the entrance of which is controlled by the solenoid value EV1 and the discharge of which is controlled by solenoid valve EV2.

An example of an artificial ventilation device has the following parameters values:
- Volume VC of tank or chamber 14 : two liters
- Compressed air supply : up to three bars
- Tidal volume insufflated : from 0 to 1.5 liters in 50 milliliters increments
- Insufflation pressure between 0 and 120 cm $H_2O$
- Maximum instantaneous flow achieve : 150 liters/mn
- Temperature of the insufflated respirable gaseous mixture : 37° C.
- Pressure PT1 in tank or chamber 14 measured by a 0 to 5 bar relative pressure sensor : accurate to within 0.5%
- Pressures Paw in the inspiration line and P2 in the bag 25 measured by differential pressure sensors
- A new mode pneumotachograph type flow sensor at the patient's mouth enabling measurement to be carried out in both directions, expiration and inspiration.

The maximum performance for this above defined example was obtained for a corresponding respiration frequency of 30 cycles per minute with a ratio of inspiration to expiration (I/E) of 0,2, an inspiratory time of 0.4 seconds, and a volume of one liter. The proper operation of the system is linked to the proper operation of the sensors, and the system's safety is ensured as follows.

The operation of the pressure sensor 32 measuring the pressure of the tank or chamber 14 during the filling stage is monitored by the system. If the signal which it outputs is not increasing, solenoid valve EV1 15 is closed and an alarm is triggered. At the differential pressure sensor 34 for measuring the airway pressure, a simple alarm is triggered in the event of 0 or no variation of the signal. A condition such as this would not give rise to a major disturbance of the operation of the system.

With regard to flow sensor 27, a fault in this sensor may cause minimum ventilation on the basis of apnea safety. If no inspiration is detected after ten seconds, insufflation is triggered with a prefilled receiver chamber 14 filled at a certain set pressure of gaseous fluid. This being the case, to prevent problems associated with leakage or a disconnection phenomenon, a table of equivalence between the insufflated volume and a theoretical field pressure is prepared. In addition, the difference *p between the fluid pressure and the theoretical pressure is measured. If a disconnection, voluntary or accidental, occurs before the flow meter 21, and if the patient has low or weak natural spontaneous ventilation, an increase in the box fill pressure would occur such as to increase the tidal volume. This increase is voluntarily limited by measuring the difference ▲ p.

If ▲ p corresponds to a variation in the fill pressure that is 10% above the theoretical value, the latter serves as a set point. As a result, all risk of hyper-insufflation associated with the increase in field pressure are excluded.

Other problems may also arise in the event of leaks in the lines or in other portions of the device. To compensate for such leaks, an upstream leak will be counteracted by an increase in the field pressure PT1 in order to supply the minimum current tidal volume. A leak downstream of the flow meter on the other hand will be detected by comparing insufflated and expired volumes.

Finally, the close loop control and control data processing system will be monitored, and if it is out of order, an alarm will be triggered and the system will remain open in spontaneous ventilation.

We claim:

1. An artificial ventilation device for a patient on a ventilatory cycle comprising inspiration and expiration, said ventilation device comprising:

closed loop control means for automatically changing said ventilation device to one of three modes of ventilation, a first mode comprising spontaneous ventilation, wherein a patient on said ventilation device completely controls ventilation and achieves an optimum minute volume value, a second mode comprising assisted ventilation, wherein a patient receives assistance from said ventilation device so as to achieve said optimum minute volume value, and a third mode comprising totally controlled ventilation, wherein said ventilation device controls a plurality of breathing parameters so as to achieve said optimum minute volume value, said optimum minute volume value being a theoretically satisfactory value set by an operator of said ventilation device as a function of the patient's condition and natural spontaneous breathing;

piping means for piping a gaseous fluid to the patient, said piping means comprising entering means for entering breathing parameter reference settings suitable for fixing said optimum minute volume value, said reference settings comprising a respiratory rate and a minimum tidal volume, said reference settings fixing said optimum minute volume value by means of an equation Vmnopt=RR×VTtot, whereby Vmnopt is the optimum minute volume value, RR is the respiratory rate, and VTtot is the sum of the patient's spontaneous tidal volume VTpat and a tidal volume which is delivered by said ventilation device VTmach, i.e. the total tidal volume, said closed loop control means controlling the total tidal volume value VTtot delivered to the patient;

and means for monitoring said total tidal volume delivered to the patient in each cycle, said closed loop control means checking the equation by means of said monitoring means and said reference settings to determine whether the patient is achieving said optimum minute volume value, thereby determining the proper mode of ventilation for the patient, from among said first mode, wherein VTmach=0, said second mode, wherein both VTmach≠0 and VTpat≠0, and said third mode, wherein VTpat=0, and configuring the ventilation device into the proper mode of ventilation.

2. The artificial ventilation device according to claim 1, further comprising means for delivering maximum assistance to the patient at the start of inspiration, i.e., when the patient is at low pulmonary volume, and for delivering assistance during the inspiration phase on insufflation by said artificial device.

3. The artificial ventilation device according to claim 2, further comprising means for measuring the rate of fluid inspired and/or expired by the patient, said measuring means being placed upstream of the patient and producing a flow signal.

4. The artificial ventilation device according to claim 3, further comprising means for processing said flow signal measured in order to detect instants of zero flow at the end of at least one of inspiration and expiration phases and to determine the total tidal volume VTtot inspired by the patient as a function of the rate of flow measured.

5. The artificial ventilation device according to claim 1, further comprising means for changing the amount of respiratory assistance and for adjusting the pressurized fluid supply to ensure that said equation is satisfied, said adjustment being made as a function of the patient's own natural spontaneous supply of respirable gaseous fluid.

6. The artificial device according to claim 2, wherein said piping means comprises an inspiration line and further wherein said setting means comprise:
- a receiving chamber, having a predetermined volume, inserted in said inspiration line at a position between said pressurized supply and the patient, said chamber being filled with pressurized gaseous fluid in each respiratory cycle, at a predetermined working pressure; and
- discharge means for discharging said pressurized gaseous fluid, said discharge means located downstream of said chamber, in order to empty gaseous fluid from said chamber suddenly and produce a peak in the fluid flow rate at the start of insufflation.

7. The artificial ventilation device according to claim 1, further comprising solenoid valves for circulating gaseous fluid in said artificial ventilation device, said solenoid valves being connected to said piping means, said device further comprising:
- calculation and control means having a central processing unit for controlling the sequential performance of various functions;
- an interface for collecting reference setting values, including one or more of optimum ventilation volume per minute, minimum tidal volume, maximum airway pressure, and maximum respiratory frequency, and measured information including one or more of working pressure in said chamber, airway pressure, inspiration pressure, and expiration pressure; and
- an output interface for monitoring the sequential control of said solenoid valves to authorize on of a plurality of modes including spontaneous ventilation, total control ventilation, and a third mode including one or both of an intermediate artificial ventilation and an expiration phase.

8. A method for providing artificial ventilation to a patient on a ventilatory cycle comprising inspiration and expiration, said method comprising:
- automatically choosing between three modes of ventilation, a first mode comprising spontaneous ventilation, wherein a patient on said ventilation device completely controls ventilation and achieves an optimum minute volume value, a second mode comprising assisted ventilation, wherein a patient receives assistance from said ventilation device so as to achieve said optimum minute volume value, and a third mode comprising totally controlled ventilation, wherein said ventilation device controls a plurality of breathing parameters so as to achieve said optimum minute volume value, said optimum minute volume value being a theoretically satisfactory value set by an operator as a function of the patient's condition and natural spontaneous breathing;
- piping a gaseous fluid to the patient;
- entering breathing parameter reference settings suitable for fixing said optimum minute volume value, said reference settings comprising a respiratory rate and a minimum total volume, said reference settings fixing said optimum minute volume value by means of an equation $Vmnopt = RR \times VTtot$, whereby Vmnopt is the optimum minute volume value, RR is the respiratory rate, and VTtot is the sum of the patient's spontaneous tidal volume VTpat and a tidal volume which is delivered by said ventilation device VTmach, i.e. the total tidal volume;
- controlling the total tidal volume value VTtot delivered to the patient;
- monitoring said total tidal volume delivered to the patient in each cycle;
- checking the equation in view of the monitored total tidal volume and said reference settings to determine whether the patient is achieving said optimum minute volume value;
- determining the proper mode of ventilation for the patient, among said first mode, wherein $VTmach = 0$, said second mode, wherein both $VTmach \neq 0$ and $VTpat \neq 0$, and said third mode, wherein $VTpat = 0$;
- and configuring the ventilation mode into the proper mode of ventilation.

9. The method for providing artificial ventilation to a patient according to claim 8, further comprising, on insufflation during an inspiration phase of the patient, delivering maximum assistance at the start of inspiration when said patient has a small pulmonary volume.

10. The method according to claim 9, wherein in each inspiration phase, when the method is in an artificial ventilation mode, the patient is insufflated with a discharge of a given volume of respirable gaseous fluid which was first brought to a preset working pressure.

11. The method according to claim 8, wherein a cycle cut-off is controlled in the inspiratory and expiratory phases in accordance with detected amounts of zero flow at the end of inspiration and at the end of expiration by the patient.

12. The method according to claim 8, wherein if the patient controls said patient parameters to satisfy said equation, inspiratory assistance is de-activated, whereas if without inspiratory assistance said patient parameters do not satisfy said equation, the amount of inspiratory assistance is increased during each cycle until such time as said patient parameters satisfy said equation with the help of inspiratory assistance.

13. The method according to claim 12, wherein when desired breathing parameters, which are parameters which satisfy said equation, are reached with the help of inspiratory assistance, the amount of inspiratory assistance is progressively decreased while, at the same time, a closed loop control is maintained in said controlling step until such time as the patient achieves a spontaneous ventilation mode.

14. The method according to claim 8, wherein a maximum value of respiratory rate is set to prevent the risk of hyperventilation.

15. An artificial ventilation device for a patient on a ventilatory cycle comprising inspiration and expiration, said ventilation device comprising:
- closed loop control means for automatically changing said ventilation device to one of a plurality of modes of ventilation, said plurality of modes including a first mode, comprising a spontaneous ventilation mode wherein a patient on said ventilation device completely controls ventilation and achieves an optimum minute volume value, and a second mode comprising a totally controlled ventilation mode wherein said ventilation device controls a plurality of breathing parameters so as to achieve said optimum minute volume value;

said optimum minute volume value being a theoretically satisfactory value set by an operator of said ventilation device as a function of the patient's condition and natural spontaneous breathing;

piping means for piping a gaseous fluid to the patient, said piping means comprising entering means for entering breathing parameter reference settings suitable for fixing said optimum minute volume value, said reference settings comprising a respiratory rate and a magnum tidal volume, said reference settings fixing said optimum minimum volume value by means of an equation $Vmnopt = RR \times VTtot$, whereby Vmnopt is the optimum minute volume value, RR is the respiratory rate, and VTtot is the sum of the patient's spontaneous tidal volume VTpat and a tidal volume which is delivered by said ventilation device VTmach, i.e. the total tidal volume;

said plurality of modes being determined by the values of VTmach and VTpat, respectively;

said closed control means controlling the total tidal volume value VTtot delivered to the patient;

means for monitoring said total tidal volume delivered to the patient; and means for monitoring said total volume delivered to the patient in each cycle, said closed loop control means checking the equation by means of said monitoring means and said reference settings to determine whether the patient is achieving said optimum minute volume value, thereby determining the proper mode of ventilation for the patient, among said plurality of modes, and configuring the ventilation device into the proper mode of ventilation.

16. A method for providing artificial ventilation to a patient on a ventilatory cycle comprising inspiration and expiration, said method comprising:

automatically choosing between a plurality of modes of ventilation, said plurality of modes comprising a first mode of spontaneous ventilation, wherein a patient on said ventilation device completely controls ventilation and achieves an optimum minute volume value, a second mode of totally controlled ventilation, wherein said ventilation device controls a plurality of breathing parameters so as to achieve said optimum minute volume value, said optimum minute volume value being a theoretically satisfactory value set by an operator as a function of the patient's condition and natural spontaneous breathing;

piping a gaseous fluid to the patient;

entering breathing parameter reference settings suitable for fixing said optimum minute volume value, said reference settings comprising a respiratory rate and a minimum tidal volume, said reference settings fixing said optimum minute volume value by means of an equation $Vmnopt = RR \times VTtot$, whereby Vmnopt is the optimum minute volume value, RR is the respiratory rate, and VTtot is the sum of the patient's spontaneous tidal volume VTpat and a tidal volume which is delivered by said ventilation device VTmach, i.e. the total tidal volume;

controlling the total tidal volume value VTtot delivered to the patient;

monitoring said total tidal volume delivered to the patient in each cycle;

checking the equation in view of the monitored total tidal volume and said reference settings to determine whether the patient is achieving said optimum minute volume value;

determining the proper mode of ventilation for the patient, among said plurality of modes which are determined by the values of VTmach and VTpat, respectively;

choosing between said modes, by determining the appropriate value of VTmach; and changing the ventilation mode into the proper mode of ventilation.

* * * * *